United States Patent [19]

Barberich et al.

[11] Patent Number: 5,190,962
[45] Date of Patent: Mar. 2, 1993

[54] TREATING HYPERTENSION

[75] Inventors: Timothy J. Barberich, Concord; James W. Young, Still River, both of Mass.

[73] Assignee: Sepracor, Inc., Marlborough, Mass.

[21] Appl. No.: 492,647

[22] Filed: Mar. 13, 1990

[51] Int. Cl.$^5$ .................... A61K 31/44; A61K 31/215
[52] U.S. Cl. ...................................... 514/356; 514/529
[58] Field of Search .................................. 514/356, 529

[56] References Cited

U.S. PATENT DOCUMENTS 4,582,840  4/1986  Garthoff et al. ..................... 514/356
4,724,141  2/1988  Schmidt et al. ..................... 514/356

OTHER PUBLICATIONS

*Chemical Abstracts* 1983, 98(1): 317g, Kazda et al., Antihypertensive Effect of Calcium Antagonists in Rats Differs from that of Vasodilators.

*Cardiologia* 1987 32(9): 1047–1052, Thomas et al.

A. C. Mann and M. M. Hosey, *Circulation Research*, 61(3):379–388 (1987).

D. Rampe et al., *Canadian J. Phys. Pharmacol.*, 65(7):1452–1459 (1987).

J. K. Saha et al., *Canadian J. Phys. Pharmacol.*, 67(7):780–794 (1989).

*Primary Examiner*—Stanley J. Friedman
*Attorney, Agent, or Firm*—Hamilton, Brook, Smith & Reynolds

[57] ABSTRACT

The optically pure isomer of nitrendipine having antihypertensive activity, is a potent anti-hypertensive drug for reducing blood pressure in individuals without the undesirable side effects associated with administration of a racemic mixture of nitrendipine. A method is disclosed utilizing an optically pure isomer of nitrendipine for treating hypertension while reducing undesirable side effects associated with nitrendipine.

1 Claim, No Drawings

TREATING HYPERTENSION

BACKGROUND

Nitrendipine is a drug belonging to the general class of compounds known as dihydropyridine calcium channel blockers. This class of drugs has the property of inhibiting the transmembrane influx of calcium ions into cardiac muscle and smooth muscle without changing serum calcium concentrations. The contractile processes of cardiac muscle and vascular smooth muscle are dependent upon the movement of extracellular calcium ions into these cells through specific ion channels. Nitrendipine relaxes coronary vascular smooth muscle, and exerts its hypotensive effect at drug levels which cause little or no weakening of cardiac contractions.

Nitrendipine is presently administered as a racemic mixture. That is, it is a mixture of optical isomers, called enantiomers. Enantiomers are structurally identical compounds which differ only in that one isomer is a mirror image of the other and the mirror images cannot be superimposed. This phenomenon is known as chirality. Most biological molecules exist as enantiomers and exhibit chirality. Although structurally identical, enantiomers can have profoundly different effects in biological systems: one enantiomer may have a specific biological activity while the other enantiomer has no biological activity at all, or may have an entirely different form of biological activity.

SUMMARY OF THE INVENTION

The present invention relates to a method of treating hypertension in an individual, comprising administering to the individual a therapeutically effective amount of an optically pure enantiomer of nitrendipine which has anti-hypertensive activity. The optically pure enantiomer is substantially free of the other enantiomer which lacks or has a lower level of such activity. The method is useful in treating hypertension while reducing or avoiding undesirable side effects, such as headache, flushing, dizziness, weakness, and peripheral edema which are often associated with administration of a racemic mixture of nitrendipine. In these applications, it is important to have an anti-hypertensive composition which minimizes these side effects. A composition containing the optically pure isomer of nitrendipine having anti-hypertensive activity is particularly useful for this application because this isomer exhibits both of these desired characteristics.

The present method provides a safe, highly effective method for treating severe hypertension while reducing undesirable side effects associated with anti-hypertensive drugs, including the racemic mixture form of nitrendipine.

DETAILED DESCRIPTION OF THE INVENTION

The present invention relies on the calcium channel blocking activity of an optically pure enantiomer of nitrendipine to provide enhanced calcium channel centagonist activity, for example, for treatment or prevention of hypertension, while simultaneously reducing many of the undesirable side effects associated with anti-hypertensive drugs including the racemic mixture of nitrendipine. Such side effects include headache, flushing, dizziness, weakness and peripheral edema. In the present method, the optically pure isomer of nitrendipine which exhibits anti-hypertension activity is administered alone, or in combination with other drugs in adjunctive treatment to an individual suffering from hypertension. The optically pure isomer of nitrendipine as used herein refers to the optically pure isomer of ethyl,methyl 1,4-dihydro-2,6-dimethyl-4-(m-nitrophenyl)-3, 5-pyridine-dicarboxylate which has anti-hypertensive activity, and to any biologically acceptable form thereof, such as a salt or ester of this compound. The term "optically pure" as used herein means that the nitrendipine composition contains at least 90% by weight of the isomer of nitrendipine having anti-hypertensive activity and 10% by weight or less of the other isomer. Optically pure nitrendipine is obtainable by purification from racemic nitrendipine and/or by asymmetric synthetic techniques by methods known to those of skill in the art.

In the present method, the optically pure isomer of nitrendipine is administered to an individual suffering from hypertension. For example, nitrendipine is administered therapeutically to an individual to reduce or ameliorate hypertension. In another embodiment, optically pure nitrendipine can be administered prophylactically to reduce the probability of occurrence of hypertension.

The drug can be administered orally, by subcutaneous or other injection, intravenously, topically, parenterally, transdermally, rectally or via by sustained release methods, e.g., an implanted reservoir containing the optically pure active isomer of nitrendipine. The form in which the drug will be administered (e.g., powder, tablet, capsule, solution, emulsion) will depend on the route by which it is administered. The quantity of the drug to be administered will be determined on an individual basis, and will be based at least in part on consideration of the individual's size, the severity of the symptoms to be treated and the result sought. In general, a therapeutically effective amount, which is the quantity of optically pure nitrendipine sufficient to reduce hypertension will be administered As used herein, the term "reduce" means to lessen or eliminate hypertension. For example, from about 30 mg to about 120 mg per day of the optically pure isomer of nitrendipine per day, given in one dose, or in two or more doses during the day, will be adequate in most individuals to produce the desired effect. Typically, a dose of about 10 mg to about 40 mg per day, will be administered three times daily.

In the method of the present invention, the optically pure isomer of nitrendipine can be administered along with one or more additional drugs. For example, other anti-hypertensive agents, such as thiazide-type diuretics and beta blockers, can be given with or in close temporal proximity to administration of optically pure nitrendipine. The two (or more) drugs (optically pure nitrendipine and another drug) can be administered in one composition or as two separate entities. For example, they can be administered in a single capsule, tablet, powder, liquid, etc. or as individual compounds. The components included in a particular composition, in addition to optically pure nitrendipine, and another drug or drugs, are determined primarily by the manner in which the composition is to be administered. For example, a composition to be administered orally in tablet form can include, in addition to the drugs, a filler (e.g., lactose), a binder (e.g., carboxymethyl cellulose, gum arabic, gelatin), an adjuvant, a flavoring agent, a coloring agent and a coating material (e.g., wax or a plasticizer). A composition to be administered in liquid form can include the combination of drugs and, optionally, an emulsifying agent, a flavoring agent and/or a coloring agent.

In general, according to the method of the present invention, optically pure nitrendipine, alone or in combination with another drug(s), is administered to an individual periodically as necessary to reduce or ameliorate symptoms of hypertension being treated while reducing or avoiding undesirable side effects, associated with racemic nitrendipine including headache, flushing, dizziness, weakness and peripheral edema. The length of time during which the drugs are administered and the dosage will depend on the disorder being treated, the type and severity of the symptoms, and the physical condition of the individual being treated.

EQUIVALENTS

Those skilled in the art will recognize, or be able to ascertain, using no more than routine experimentation, many equivalents to the specific embodiments of the invention described herein. Such equivalents are intended to be encompassed in the scope of the following claims.

We claim:
1. A method of treating hypertension in an individual with nitrendipine and reducing undesirable side effects associated with administration of nitrendipine, comprising administering to the individual a therapeutically effective amount of optically pure nitrendipine which has anti-hypertensive activity and at least one additional drug selected from the group consisting of a thiazole diuretic and a beta blocker.

* * * * *

UNITED STATES PATENT AND TRADEMARK OFFICE
CERTIFICATE OF CORRECTION

PATENT NO. : 5,190,962
DATED : March 2, 1993
INVENTOR(S) : Timothy J. Barberich and James W. Young It is certified that error appears in the above-identified patent and that said Letters Patent is hereby corrected as shown below:

On the title page,
Please amend the title to: ---Method of Treating Hypertension With Optically Pure Nitrendipine---

Column 1, lines 60-61: delete "centagonist" and insert ---antagonist---

Column 2, line 27: after "via", delete "by"

Claim 1, line 16: delete "thiazole" and insert ---thiazole-type---.

Signed and Sealed this

Eighteenth Day of January, 1994

Attest:

BRUCE LEHMAN

Attesting Officer
Commissioner of Patents and Trademarks